United States Patent
Dale et al.

(10) Patent No.: US 6,211,349 B1
(45) Date of Patent: Apr. 3, 2001

(54) PROTONATED/ACIDIFIED NUCLEIC ACIDS AND METHODS OF USE

(75) Inventors: Roderic M. K. Dale, Wilsonville, OR (US); Amy Arrow, Bethel, ME (US); Steven L. Gatton, Lake Oswego; Terry Thompson, West Linn, both of OR (US)

(73) Assignee: Oligos Etc., Inc., Wilsonville, OR (US)

( * ) Notice: Subject to any disclaimer, the term of this patent is extended or adjusted under 35 U.S.C. 154(b) by 0 days.

(21) Appl. No.: 09/222,009

(22) Filed: Dec. 30, 1998

(51) Int. Cl.[7] ............................ C07H 21/02; C07H 21/04; C07H 19/00
(52) U.S. Cl. ................ 536/23.1; 536/23.5; 536/24.1; 536/24.2; 536/24.33; 536/28.2
(58) Field of Search .......................... 536/23.5, 23.1, 536/28.2; 435/6; 514/44; 424/1.13

(56) References Cited

U.S. PATENT DOCUMENTS

| | | | |
|---|---|---|---|
| 5,294,533 | 3/1994 | Lupski et al. | 435/6 |
| 5,747,256 * | 5/1998 | Yan et al. | 435/6 |

FOREIGN PATENT DOCUMENTS

WO 96/29399   9/1996   (WO) .

OTHER PUBLICATIONS

Heidenreich et al., Molecular Medicine Today, vol. 1, p. 128–133, 1995.*
Mastrangelo et al., Seminars in Oncology, vol. 23 (1), p. 4–21, Feb. 1996.*
Verma et al., Nature, vol. 389, p. 239–242, Sep. 1997.*
Eck et al., Goodman & Gilman's The Pharmacological Basis of THerapeutics, Ninth Edition, McGraw–Hill, New York, p. 77–101, 1996.*
Zimmer et al., Biopolymers, vol. 6(4), 563–574, 1968.*
Archer et al., 1994, *Antimicrob. Agents Chemother.* 38:2231–2237.
Bennett, 1993, *Antisense Res. Devel.* 3:235–241.
Cohen, 1989, *Oligodeoxynucleotides; Antisense Inhibitors of Gene Expression*, Boca Raton, FL, CRC Press.
Crooke, 1997, in *Antisense Nucleic Acid and Antisense RNA: Novel Pharmacological and Therapeutic Agents*, B. Weiss ed., CRC Press Boca Raton, FL., p. 17.
Goth, 1974, *Medical Pharmacology: Principles and Concepts*, The C.V. Mosby Company, Saint Louis, MO.
Hoke et al., 1991, *Nucl. Acids Res.* 19–5743.
Hughes et al., 1995, *Pharmaceutical Research* 12:817.
Krieg et al., 1995, *Nature* 374:546–549.
Kristinsson, 1995, *Microb. Drug Resistance* 1(2):121.
Woodford et al., 1995, *J. Antimicrob. Chemother.* 35:179–184.
Yamamoto et al., 1994, *Antisense Res. Devel.* 4:119–122.
Zabransky et al., 1995, *J. Clin. Microbiol.* 33(4):791–793.

* cited by examiner

Primary Examiner—Karen M. Hauda
Assistant Examiner—Shin-Lin Chen
(74) Attorney, Agent, or Firm—Bozicevic, Field & Francis LLP; Dianna L. DeVore

(57) ABSTRACT

The novel discovery that protonated nucleic acids inhibit bacterial growth is reported and methods for the preparation and therapeutic use of nuclease resistant and acid resistant protonated/acidified nucleic acids for administration to animals including man, to treat or prevent a bacterial infection are described.

19 Claims, No Drawings

SEQUENCE LISTING

```
<160> NUMBER OF SEQ ID NOS: 9

<210> SEQ ID NO 1
<211> LENGTH: 9
<212> TYPE: DNA
<213> ORGANISM: Artificial Sequence
<220> FEATURE:
<223> OTHER INFORMATION: Synthesized Oligonucleotide

<400> SEQUENCE: 1 cgccattgg                                                                 9

<210> SEQ ID NO 2
<211> LENGTH: 6
<212> TYPE: DNA
<213> ORGANISM: Artificial Sequence
<220> FEATURE:
<223> OTHER INFORMATION: Synthesized Oligonucleotide

<400> SEQUENCE: 2 cgccat                                                                    6

<210> SEQ ID NO 3
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 3
acgcgccatt gg                                                            12

<210> SEQ ID NO 4
<211> LENGTH: 21
<212> TYPE: DNA
<213> ORGANISM: Artificial Sequence
<220> FEATURE:
<223> OTHER INFORMATION: Synthesized Oligonucleotide

<400> SEQUENCE: 4
ggaacgcgcc attggtatat c                                                  21

<210> SEQ ID NO 5
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 5
aaaaaaaaaa aa                                                            12

<210> SEQ ID NO 6
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 6
```

```
uuuuuuuuuu uu                                                           12

<210> SEQ ID NO 7
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 7
gggggggggg gg                                                           12

<210> SEQ ID NO 8
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 8
cccccccccc cc                                                           12

<210> SEQ ID NO 9
<211> LENGTH: 12
<212> TYPE: DNA
<213> ORGANISM: Artificial Sequence
<220> FEATURE:
<223> OTHER INFORMATION: Synthesized Oligonucleotide

<400> SEQUENCE: 9
acgcgccatt at                                                           12
```

PROTONATED/ACIDIFIED NUCLEIC ACIDS AND METHODS OF USE

FIELD OF THE INVENTION

The invention relates generally to the field of modified nucleic acids and more specifically to nucleic acids used as antibiotic agents.

BACKGROUND TO THE INVENTION

Pathogenic bacteria responsible for infectious diseases were once thought to be controllable through the use of a battery of antibiotics such as penicillin, streptomycin, tetracycline, and others. However, since the widespread use of antibiotics began in the 1950s, more and more bacteria have evolved to become resistant to one or more antibiotics. Multiple drug-resistant strains are increasingly common, particularly in hospitals.

Currently, nosocomial Staphylococcal infections exhibit multiple drug resistance. See, for example Archer et al., 1994, *Antimicrob. Agents Chemother.* 38:2231–2237. At this time, the remaining antibiotic that demonstrates the ability to kill most strains of Staphylococci is vancomycin. However, vancomycin resistant strains of both Staphylococcus and Enterococcus have already been isolated and reported by Zabransky et al., 1995, *J. Clin. Microbiol.* 33(4):791–793. Furthermore, transfer of resistance from Enterococci to Staphylococci has been previously documented by Woodford et al., 1995, *J. Antimicrob. Chemother.* 35:179–184. *Streptococcus pneumoniae* is a leading cause of morbidity and mortality in the United States (*M.M.W.R.*, Feb. 16, 1996, Vol. 45, No. RR-1). Each year these bacteria cause 3,000 cases of meningitis, 50,000 cases of bacteremia, 500,000 cases of pneumonia, and 7,000,000 cases of otitis media. Case fatality rates are greater than 40% for bacteremia and greater than 55% for meningitis, despite antibiotic therapy. In the past, *Streptococcus pneumoniae* were uniformly susceptible to antibiotics; however, antibiotic resistant strains have emerged and are becoming widespread in some communities.

In addition, there are instances where antibiotic resistance is not an issue, yet a particular bacteria remains refractory to treatment using conventional antibiotics. Such is the case with *Escherichia coli* 0157:H7, a causative agent for food poisoning and death from undercooked meat. The Department of Agriculture estimates that 10 people die each day and another 14,000 become ill due to this bacteria. Unfortunately, conventional antibiotics are completely ineffective against this organism.

The history of antibiotic treatment of pathogenic bacteria is cyclical. Bacteria are remarkably adaptive organisms, and, for each new antibiotic that has been developed, resistant bacterial strains arise through the widespread use of the antibiotic. Thus, there is a constant need to produce new antibiotics to combat the next generation of antibiotic-resistant bacteria. Traditional methods of developing new antibiotics have slowed, and in the past two years only one new antibiotic has been approved by the FDA. Furthermore, according to Kristinsson (*Microb. Drug Resistance* 1(2):121 (1995)), "there are no new antimicrobial classes with activity against resistant Gram positives on the horizon."

Antisense therapy uses nucleic acids to specifically inhibit unwanted gene expression in cells. Antisense nucleic acids can be used to hybridize to and inhibit the function of an RNA, typically messenger RNA, by activating RNase H or physically blocking the binding of ribosomes or proteins, thus preventing translation of the mRNA. Antisense nucleic acids also include RNAs with catalytic activity (ribozymes), which can selectively bind to complementary sequences on a target RNA and physically destroy the target by mediating a cleavage reaction.

Antisense nucleic acids that bind to the DNA at the correct location can also prevent the DNA from being transcribed into RNA. These antisense nucleic acids are believed to bind to double-stranded DNA (forming triple-stranded DNA) and thereby inhibit gene expression.

Nucleic acids have also found use as aptamers in which their mode of action is the result of interactions with molecules other than DNAs or RNAs, e.g., proteins.

Nucleic acids have also been shown to stimulate the immune system in response to the presence of a CG motif (Yamamoto et al., 1994, *Antisense Res. Devel.* 4:119–122; Krieg et al., 1995, *Nature* 374:546–549). The mechanism of this stimulation is not clear but it does not seem to involve an antisense mechanism.

It has been demonstrated that the fate of internalized nucleic acids is critical to the success of nucleic acid therapy (Bennett, 1993, *Antisense Res. Devel.* 3:235–241). The rapid intracellular degradation of nucleic acids can be a barrier to their use. One of the major problems in utilizing naturally occurring phosphodiester nucleic acids is their rapid degradation by nucleases in mammalian cells or in serum-containing culture medium (Cohen, 1989, *Oligodeoxynucleotides; Antisense Inhibitors of Gene Expression,* Boca Raton, Fla., CRC Press). There is abundant evidence that modification of the backbone of nucleic acids confers varying degrees of nuclease resistance. Hoke et al., 1991, *Nucl. Acids Res.* 19:5743, compared phosphodiester backbone nucleic acids to fully modified phosphorothioate backbone nucleic acids and to chimeric phosphodiester and phosphorothioate backbone nucleic acids. Hoke et al. demonstrated that the phosphorothioate nucleic acids were degraded up to 45 times slower than the phosphodiester or chimeric backbone nucleic acids.

There have been reports that chimeric nucleic acids that are end-capped with nuclease resistant backbone linkages are resistant to degradation (Cohen, 1989, *Oligodeoxynucleotides: Antisense Inhibitors of Gene Expression,* Boca Raton, Fla., CRC Press). However, Hoke et al. teaches that capped nucleic acids are rapidly degraded by intracellular endonucleases, and thus capping nucleic acids with nuclease resistant modifications may not be sufficient for sustaining pharmacological activities of nucleic acids in cells. Finally, Hoke et al. concludes that while capping of nucleic acids may provide protection from exonucleases in cell culture, the action of intracellular endonucleases is sufficient to degrade these capped nucleic acids when they enter a cell.

Another limitation on the therapeutic uses of nucleic acids has been their poor bioavailability. Oral bioavailability can be affected by acid degradation in the gut, enzymatic cleavage in the intestines, poor intestinal absorption and liver first pass effects (Hughes et al., 1995, *Pharmaceutical Research* 12:817). Crooke reported very limited (<5%) bioavailability of nucleic acids in rodents (S. Crooke, 1997, in *Antisense Nucleic Acid and Antisense RNA: Novel Pharmacological and Therapeutic Agents,* B. Weiss ed., CRC Press Boca Raton, Fla., p. 17). The normal pH of the gastric hydrochloric acid (HCl) in the stomach is between 1 and 2 (A. Goth, 1974, *Medical Pharmacology: Principles and Concepts,* The C. V. Mosby Company, Saint Louis, Mo.). Nucleic acids are sensitive to acid depurination and cleavage of the DNA or RNA backbone. Exposure of nucleic acids for as short a time as 10 minutes at room temperature at a pH of 1–2 will cause depurination.

The sole effort to use nucleic acids as antibiotics to date has involved their use as antisense molecules targeted to hybridize and inhibit expression of specific bacterial genes, thereby inhibiting bacterial growth. See Lupski et al., U.S. Pat. No. 5,294,533 ('533 patent) and PCT publication NO. WO 96/29399. Although this method can be effective, it is limited in its scope of use, the strength of the effect, and the use of an antisense molecule is limited to a particular targeted organism or closely related organisms.

There is a need for a new class of broad-spectrum antibiotic agents that is effective against a wide range of bacteria, including bacteria resistant to many conventional antibiotics. In addition, there is a need for such a broad-spectrum antibiotic that is non-toxic to the treated host.

SUMMARY OF THE INVENTION

The present invention provides protonated/acidified nucleic acids that are effective antibiotics against both drug-resistant and susceptible bacteria in vitro and in vivo. These modified nucleic acids are effective as bactericidal and/or bacteristatic agents without regard to the specific sequence or length of the nucleic acid molecule. The nucleic acids of the invention are protonated/acidified and may have nuclease resistant backbones, acid resistant backbones, and, in their preferred embodiment, have both acid resistant and nuclease resistant backbones. The nucleic acids of the invention are protonated/acidified to give a pH when dissolved in water of less than pH 7 to about 1, more preferably less than pH 4.5 to about 1, and even more preferably less than pH 2 to about 1.

In one embodiment, the invention provides therapeutic uses of protonated/acidified nucleic acids as antibacterial agents. Specifically, the protonated/acidified nucleic acids of the invention are effective antibacterial agents against all bacterial species and can be used either pharmaceutically or cosmetically to treat or prevent bacterial infections in humans and other animals. The preferred method of treatment comprises the administration of protonated/acidified nucleic acids to the animal in an amount sufficient to inhibit or prevent bacterial growth, to alleviate the symptom of the bacterial growth, or in an amount effective for treatment of a bacterial infection.

In another embodiment, the invention provides for the therapeutic use of nucleic acids to treat or prevent diseases involving viral infection, inflammatory diseases, cancer, fungal infections, etc., wherein said nucleic acids are additionally protonated in order to simultaneously treat or prevent a bacterial infection.

The invention further provides the use of the described antibacterial nucleic acid, in conjunction with an acceptable pharmaceutical carrier, to prepare medicinal compositions for the treatment of bacterial infections in animals, and more preferably mammals, including humans.

The invention further provides the use of the described antibacterial nucleic acid in a topical skin cream with an acceptable cosmetic carrier. Such topical skin creams may contain additives such as emollients, moisturizers, fragrance, and the like.

The invention further provides disinfectant solutions comprised of the described antibacterial nucleic acid. The disinfectant may be suitable for use on skin, due to its non-toxicity, or may be used for disinfection of a surface such as a hospital instrument.

The present invention also provides several methods to protonate/acidify nucleic acids to confer bacteristatic or bactericidal effects on pathogenic bacteria. The resulting protonated/acidified nucleic acids can be used to treat animals, including humans, that have a disease caused by a bacterial pathogen.

It is an object of the invention to use protonated/acidified nucleic acids to inhibit the growth of any bacteria, including clinically relevant pathogenic bacteria.

It is an advantage of the invention that the mechanism of action of the protonated/acidified nucleic acids appears to be relatively non-specific, allowing them to be effective against any bacterium including clinically relevant pathogenic bacteria.

It is another advantage of the invention that the protonated/acidified nucleic acids are non-toxic to a subject treated with the modified nucleic acids.

It is a further advantage that the antibacterial effectiveness of protonated/acidified nucleic acids is neither length- nor sequence-dependent.

It is a feature of the invention that the protonated/acidified nucleic acids are effective at treating a variety of ailments caused by bacterial pathogens.

These and other objects, advantages, and features of the invention will become apparent to those skilled in the art upon reading the details of the nucleic acids and uses thereof as more fully described below.

DETAILED DESCRIPTION OF THE PREFERRED EMBODIMENTS

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "bacteria" includes a plurality of bacteria species and "an oligonucleotide" may encompass a plurality of oligonucleotides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The term "nucleic acid" and "nucleic acid molecule" as used interchangeably herein, refers to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "oligonucleotide" as used herein refers to a nucleic acid molecule comprising from about 2 to about 100 nucleotides, more preferably from 2 to 80 nucleotides, and even more preferably from about 4 to about 35 nucleotides.

The term "monomer" as used herein refers to a nucleic acid molecule and derivatives thereof comprised of a single nucleotide.

The terms "modified oligonucleotide" "modified monomer" and "modified nucleic acid molecule" as used herein refer to nucleic acids with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 2'-5', or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained.

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an α-anomer of deoxyribose may be used, where the base is inverted with respect to the natural β-anomer. In a preferred embodiment, the 2'-OH of the sugar group may be altered to 2'-O-alkyl or 2'-O-alkyl-n(O-alkyl), which provides resistance to degradation without comprising affinity.

The term "acidification" and "protonation/acidification" as used interchangeably herein refers to the process by which protons (or positive hydrogen ions) are added to proton acceptor sites on a nucleic acid. The proton acceptor sites include the amine groups on the base structures of the nucleic acid and the phosphate of the phosphodiester linkages. As the pH is decreased, the number of these acceptor sites which are protonated increases, resulting in a more highly protonated/acidified nucleic acid.

The term "protonated/acidified nucleic acid" refers to a nucleic acid that, when dissolved in water at a concentration of approximately 16 $A_{260}$ per ml, has a pH lower than physiological pH, i.e., lower than approximately pH 7. Modified nucleic acids, nuclease-resistant nucleic acids, and antisense nucleic acids are meant to be encompassed by this definition. Generally, nucleic acids are protonated/acidified by adding protons to the reactive sites on a nucleic acid, although other modifications that will decrease the pH of the nucleic acid can also be used and are intended to be encompassed by this term.

The term "end-blocked" as used herein refers to a nucleic acid with a chemical modification at the molecular level that prevents the degradation of selected nucleotides, e.g., by nuclease action. This chemical modification is positioned such that it protects the integral portion of the nucleic acid, for example the coding region of an antisense oligonucleotide. An end block may be a 3' end block or a 5' end block. For example, a 3' end block may be at the 3'-most position of the molecule, or it may be internal to the 3' ends, provided it is 3' to the integral sequences of the nucleic acid.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n (O-alkyl), 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to nucleic acids that are resistant to acid degradation as compared to unmodified nucleic acids. Typically, the relative acid resistance of a nucleic acid will be measured by comparing the percent degradation of a resistant nucleic acids with the percent degradation of its unmodified counterpart (i.e., a corresponding nucleic acids with "normal" backbone, bases, and phosphodiester linkages). A nucleic acid that is acid resistant is preferably at least 1.5 times more resistant to acid degradation, at least 2 times more resistant, even more preferably at least 5 times more resistant, and most preferably at least 10 times more resistant than their unmodified counterpart.

The term "$LD_{50}$" as used herein is the dose of an active substance that will result in 50 percent lethality in all treated experimental animals. Although this usually refers to invasive administration, such as oral, parenteral, and the like, it may also apply to toxicity using less invasive methods of administration, such as topical applications of the active substance.

The term "alkyl" as used herein refers to a branched or unbranched saturated hydrocarbon chain containing 1–6 carbon atoms, such as methyl, ethyl, propyl, tert-butyl, n-hexyl and the like.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing a bacterial disease from occurring in a subject which may be predisposed to the disease but has not yet been diagnosed as having it;

(b) inhibiting a bacterial disease, i.e., arresting its development; or (c) relieving a bacterial disease, i.e., causing regression and/or amelioration of the disease. The invention is directed toward treating patients with any infectious bacteria.

The Invention in General

This invention is based on the discovery that protonated/acidified nucleic acids of any sequence and any length represent a new class of antibiotics effective against both drug-resistant and antibiotic susceptible bacteria in vitro and in vivo. Specifically, protonated/acidified nucleic acids of the invention are effective antibacterial agents against all bacterial species, and can be used to treat or prevent bacterial infection in people and animals. Thus, the present invention includes protonated, nuclease resistant nucleic acids and methods of producing them to be effective at killing bacteria or inhibiting bacterial growth. In particular, the present invention specifically relates to the process of protonation to facilitate the antibacterial action of nucleic acids against pathogenic bacteria.

In addition, nucleic acids presently used therapeutically for the treatment of other diseases or disorders, e.g., antisense nucleic acids targeted to a specific gene, can also be protonated/acidified, thereby conferring the additional therapeutic effect of anti-bacterial activity on such nucleic acids. Thus, the present invention also includes the use of nucleic acids to treat or prevent diseases involving viral infection, cancer, fungal infections, etc., that are additionally protonated in order to simultaneously treat or prevent a bacterial infection.

Protonation/acidification can be utilized to confer on a nucleic acid the ability to function as an antibacterial agent. Acidification of nucleic acids is the process by which protons (or positive hydrogen ions) are added to the reactive sites on a nucleic acid. As the number of reactive sites that are protonated increases, the pH is decreased, and the bacterial inhibiting activity of the nucleic acid is increased. Accordingly, the nucleic acids of the invention are protonated/acidified to give a pH when dissolved in water of less than pH 7 to about pH 1, or in preferred embodiments, pH 6 to about 1 or pH 5 to about 1. In other preferred embodiments, the dissolved nucleic acids have a pH from pH 4.5 to about 1 or, in a preferred embodiment, a pH of 4.0 to about 1, or, in a more preferred embodiment, a pH of 3.0 to about 1, or, in another more preferred embodiment, a pH of 2.0 to about 1.

In a preferred embodiment, the protonated/acidified nucleic acids of the compositions and methods of the invention are substantially nuclease resistant, substantially acid resistant, and preferably, both substantially nuclease resistant and substantially acid resistant. This embodiment includes nucleic acids completely derivatized by phosphorothioate linkages, 2'-O-methyl-phosphodiesters, 2'-O-alkyls, 2'-O-alkyl-n(O-alkyl)s, 2'-fluoros, 2'-deoxy-erythropentofuranosyls, p-isopropyl nucleic acids, phosporamidates, chimeric linkages, and any other backbone modifications. This embodiment also includes other modifications that render the nucleic acids substantially resistant to endogenous nuclease activity. Methods of rendering a nucleic acid nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acids comprising the modified bases are rendered substantially nuclease resistant.

In the most preferred embodiment the protonated/acidified nucleic acid will have a backbone substantially resistant to acid degradation, exonuclease digestion, and endonuclease digestion.

Typically, the relative nuclease resistance of a nucleic acid can be measured by comparing the percent digestion of a resistant nucleic acid with the percent digestion of its unmodified counterpart (i.e., a corresponding nucleic acid with "normal" backbone, bases, and phosphodiester linkage). Percent degradation may be determined by using analytical HPLC to assess the loss of full length nucleic acids, or by any other suitable methods (e.g., by visualizing the products on a sequencing gel using staining, autoradiography, fluorescence, etc., or measuring a shift in optical density). Degradation is generally measured as a function of time.

Comparison between unmodified and modified nucleic acids can be made by ratioing the percentage of intact modified nucleic acid to the percentage of intact unmodified nucleic acid. For example, if, after 15 minutes of exposure to a nuclease, 25% (i.e., 75% degraded) of an unmodified nucleic acid is intact, and 50% (i.e., 50% degraded) of a modified nucleic acid is intact, the modified nucleic acid is said to be 2 times (50% divided by 25%) more resistant to nuclease degradation than is the unmodified nucleic acid. Generally, a substantially nuclease resistant nucleic acid will be at least about 1.25 times more resistant to nuclease degradation than an unmodified nucleic acid with a corresponding sequence, typically at least about 1.5 times more resistant, preferably about 1.75 times more resistant, and more preferably at least about 10 times more resistant after 15 minutes of nuclease exposure.

Percent acid degradation may be determined by using analytical HPLC to assess the loss of full length nucleic acids, or by any other suitable methods (e.g., by visualizing the products on a sequencing gel using staining, autoradiography, fluorescence, etc., or measuring a shift in optical density). Degradation is generally measured as a function of time.

Comparison between unmodified and modified nucleic acids can be made by ratioing the percentage of intact modified nucleic acid to the percentage of intact unmodified nucleic acid. For example, if, after 30 minutes of exposure to a low pH environment, 25% (i.e., 75% degraded) of an unmodified nucleic acid is intact, and 50% (i.e., 50% degraded) of a modified nucleic acid is intact, the modified nucleic acid is said to be 2 times (50% divided by 25%) more resistant to nuclease degradation than is the unmodified nucleic acid. Generally, substantially "acid resistant" nucleic acids will be at least about 1.25 times more resistant to acid degradation than an unmodified nucleic acid with a corresponding sequence, typically at least about 1.5 times more resistant, preferably about 1.75 more resistant, and more preferably at least about 10 times more resistant after 30 minutes of exposure at 37° C. to a pH of about 1.5 to about 4.5.

The presently described purified nucleic acids may be used as the sole therapeutic agent, or they may be complexed with additional antibacterial agents. For example, the described nuclease-resistant antibacterial nucleic acids may be linked to a conventional antibiotic or other chemical group that inhibits bacterial gene expression. Alternatively, the purified nucleic acids may be included in a therapeutic composition with agents designed for the alleviation of other disorders and/or symptoms, e.g., decongestants, antihistamines, anti-nausea agents, sedatives, pain relievers and the like. Additionally, the antibacterial nucleic acid may be complexed with a variety of well established compounds or structures that, for instance, further enhance the in vivo stability of the nucleic acid, or otherwise enhance its pharmacological properties (e.g., increase in vivo half-life, reduce toxicity, promote bioavailability, etc.).

The sequence of the nucleic acids of the invention may vary, as the antibacterial effect of the modified nucleic acids is not dependent on the sequence. For example, nucleic acids directed at treating a bacterial infection may be complementary to a known bacterial gene that is needed for bacterial growth. In another example, the nucleic acid of the invention may have no substantial sequence homology with any sequence in the genome of the bacterium that causes the infection being treated or prevented. In yet another example, nucleic acids directed at other therapeutic targets, e.g., viruses, cancer cells, fungal infections, may also be protonated/acidified according to the invention to function simultaneously as antibacterial agents in addition to their primary therapeutic function.

Bactericidal and/or bacteristatic activity of the nucleic acids of the invention may be measured using any number of methods available to those skilled in the art. One example of such a method is measurement of antibacterial activity through use of a MIC (minimal inhibitory concentration) test that is recognized to be predictive of in vivo efficacy for the treatment of a bacterial infection with antibiotics. The nucleic acids of the invention display antibacterial activity in this test, even without pretreatment of the bacteria to permeabilize the membrane and without PEG-modification of the nucleic acids.

Protonation/acidification of nucleic acids with a range of chemical alterations may be used in the invention, although a preferred embodiment of the present invention is a protonated/acidified nucleic acid with the chemical structure of 5'-butanol-2'-O-alkyl RNA-butanol-3' or 2' -O-alkyl-O-alkyl, that has a pH of 3 to 1 when dissolved in water. A particularly preferred embodiment of the present invention is a protonated/acidified nucleic acid with the chemical backbone structure of 5'-butanol-2'-O-methyl RNA-butanol-3', that has a pH of 3 to 1 when dissolved in water.

Nucleic Acid Synthesis

Nucleic acids can be synthesized on commercially purchased DNA synthesizers from <1 uM to >1 mM scales using standard phosphoramidite chemistry and methods that are well known in the art, such as, for example, those disclosed in Stec et al., 1984, *J. Am. Chem. Soc.* 106:6077–6089, Stec et al., 1985, *J. Org. Chem.* 50(20):3908–3913, Stec et al., 1985, *J. Chromatog.* 326:263–280, LaPlanche et al., 1986, *Nuc. Acid. Res.* 14(22):9081–9093, and Fasman, 1989 *Practical Handbook of Biochemistry and Molecular Biology*, 1989, CRC Press, Boca Raton, Fla., herein incorporated by reference.

Nucleic acids can be purified by any method known to those in the art. In a preferred embodiment, they are purified by chromatography on commercially available reverse phase or ion exchange media, e.g., Waters Protein Pak, Pharmacia's Source Q, etc. Peak fractions can be combined and the samples desalted and concentrated by means of reverse phase chromatography on a poly(styrene-divinylbenzene) based media, Hamilton's PRP1 or PRP3, or Polymer Labs' PLRP resins. Alternatively, ethanol precipitation, diafiltration, or gel filtration may be used followed by lyophilization or solvent evaporation under vacuum in commercially available instrumentation such as Savant's Speed Vac. Optionally, small amounts of the nucleic acids may be electrophoretically purified using polyacrylamide gels.

Lyophilized or dried-down preparations of nucleic acids can be dissolved in pyrogen-free, sterile, physiological saline (i.e., 0.85% saline), sterile Sigma water, and filtered through a 0.45 micron Gelman filter (or a sterile 0.2 micron pyrogen-free filter). The described nucleic acids may be partially or fully substituted with any of a broad variety of chemical groups or linkages including, but not limited to: phosphoramidates; phosphorothioates; alkyl phosphonates; 2'-O-methyl; 2'-modified RNA; morpholino groups; phosphate esters; propyne groups; or chimerics of any combination of the above groups or other linkages (or analogues thereof).

A variety of standard methods can be used to purify the presently described antibacterial nucleic acids. In brief, the antibacterial nucleic acids of the present invention can be purified by chromatography on commercially available reverse phase media (for example, see the RAININ Instrument Co., Inc. instruction manual for the DYNAMAX®-300A, Pure-DNA reverse phase columns, 1989, or current updates thereof, herein incorporated by reference) or ion exchange media such as Waters' Protein Pak or Pharmacia's Source Q (see generally, Warren and Vella, 1994, "Analysis and Purification of Synthetic Nucleic Acids by High-Performance Liquid Chromatography", in *Methods in Molecular Biology*, vol. 26; *Protocols for Nucleic acid Conjugates*, S. Agrawal, ed. Humana Press, Inc., Totowa, N.J.; Aharon et al., 1993, *J. Chrom.* 698:293–301; and Millipore Technical Bulletin, 1992, *Antisense DNA: Synthesis, Purification, and Analysis*). Peak fractions can be combined and the samples concentrated and desalted via alcohol (ethanol, butanol, isopropanol, and isomers and mixtures thereof, etc.) precipitation, reverse phase chromatography, diafiltration, or gel filtration.

A nucleic acid is considered pure when it has been isolated so as to be substantially free of, inter alia, incomplete nucleic acid products produced during the synthesis of the desired nucleic acid. Preferably, a purified nucleic acid will also be substantially free of contaminants which may hinder or otherwise mask the antibacterial activity of the oligonucleotide. A purified nucleic acid, after acidification by one of the disclosed methods or by any other method known to those of skill in the art, is a protonated/acidified nucleic acid that has been isolated so as to be substantially free of, inter alia, excess protonating/acidifying agent. In general, where a nucleic acid is able to bind to, or gain entry into, a target cell to modulate a physiological activity of interest, it shall be deemed as substantially free of contaminants that would render the nucleic acid less useful.

In particular embodiments, the nucleic acids of the invention are composed of one or more of the following: partially or fully substituted phosphorothioates, phosphonates, phosphate esters, phosphoroamidates, 2'-modified RNAs, 3'-modified RNAs, peptide nucleic acids, propynes or analogues thereof. The nucleic acids may be completely or partially derivatized by a chemical moeity including, but not limited to, phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, morpholino, bridged phosphorothioate linkages, sulfone internucleotide linkages, 3'-3' linkages, 5'-2' linkages, 5'-5' linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, p-isopropyl oligonucleotides, or phosphoramidates.

Protonated/Acidified Nucleic Acids

Subsequent to, or during, the above synthesis and purification steps, protonated/acidified forms of the described nucleic acids can be generated by subjecting the purified, or partially purified, or crude nucleic acids, to a low pH, or acidic, environment. Purified or crude nucleic acids can be protonated/acidified with acid, including, but not limited to, phosphoric acid, nitric acid, hydrochloric acid, acetic acid, etc. For example, acid may be combined with nucleic acids in solution, or alternatively, the nucleic acids may be dissolved in an acidic solution. Excess acid may be removed by chromatography or in some cases by drying the nucleic acid.

Other procedures to prepare protonated nucleic acids known to the skilled artisan are equally contemplated to be within the scope of the invention. Once the nucleic acids of the present invention have been protonated they may be separated from any undesired components like, for example, excess acid. The skilled artisan would know of many ways to separate the oligonucleotides from undesired components. For example, the oligonucleotide solution may be subjected to chromatography following protonation. In a preferred embodiment, the oligonucleotide solution is run over a poly(styrene-divinyl benzene) based resin (e.g., Hamilton's PRP-1 pr 3 and Polymer Lab's PLRP) following protonation.

The protonated/acidified nucleic acids can be used directly, or in a preferred embodiment, processed further to remove any excess acid and salt via precipitation, reverse phase chromatography, diafiltration, or gel filtration. The protonated/acidified oligos can be concentrated by precipitation, lyophilization, solvent evaporation, etc. When suspended in water or saline, the acidified nucleic acid preparations of the invention typically exhibit a pH of between 1 and 4.5 depending upon the level of protonation/acidification, which can be determined by how much acid is used in the acidification process. Alternatively, nucleic acids can be protonated by passage over a cation exchange column charged with hydrogen ions.

Acid and Nuclease Resistant Nucleic Acids

Generally, nucleic acid preparations near pH 2 to 1 demonstrate better antibacterial activity than nucleic acids at or near pH 4.5. Many oligo backbones are not stable at pH 2 and experience depurination, although a number of backbones are relatively stable at a pH of 4 to 5. It has been discovered that 2'-O-alkyl, 3'-O-alkyl, and 2'-O-alkyl-n(O-alkyl) nucleic acids are stable at the desired pH of 2 to 1.

In one embodiment, the invention uses nucleic acids that are substantially nuclease resistant. This includes nucleic acids completely derivatized by phosphorothioate linkages, 2'-O-methylphosphodiesters, 2'-O-alkyl, 2'-O-alkyl-n(O-alkyl), 2'-fluoro, 2' -deoxy-erythropentofuranosyl, p-ethoxy, morpholino nucleic acids, p-isopropyl nucleic acids, phosphoramidates, chimeric linkages, and any other backbone modifications, as well as other modifications, which render the nucleic acids substantially resistant to endogenous nuclease activity. Additional methods of rendering nucleic acids nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acids comprising the modified bases are rendered substantially nuclease resistant.

Although 2'-O-alkyl substituted nucleic acids and molecules with similar modifications exhibit marked acid stability and endonuclease resistance, they are sensitive to 3' exonucleases. In order to enhance the exonuclease resistance of 2'-O-alkyl substituted nucleic acids, the 5' and 3' ends of the ribonucleic acid sequence are preferably attached to an exonuclease blocking function. For example, one or more phosphorothioate nucleotides can be placed at either end of the oligoribonucleotide. Additionally, one or more inverted bases can be placed on either end of the oligoribonucleotide, or one or more alkyl, e.g., butanol-substituted nucleotides or chemical groups can be placed on one or more ends of the oligoribonucleotide. An enzyme-resistant butanol preferably has the structure OH—$CH_2CH_2CH_2CH_2$ (4-hydroxybutyl) which is also referred to as a C4 spacer. Accordingly, a preferred embodiment of the present invention is a protonated/acidified nucleic acid comprising an antibacterial nucleic acid having the following structure:

wherein "B" is a 2'-O-alkyl or 2'-O-alkyl-O-alkyl oligoribonucleotide between about 1 and about 78 bases in length, and "A" and "C" are respective 5' and 3' end blocking groups (e.g., one or more phosphorothioate nucleotides (but typically fewer than six), inverted base linkages, or alkyl, alkenyl, or alkynl groups or substituted nucleotides). A partial list of blocking groups includes inverted bases, dideoxynucleotides, methylphosphates, alkyl groups, aryl groups, cordycepin, cytosine arabanoside, 2'-methoxyethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen and glyceryl.

Therapeutic Use of Antibacterial Nucleic Acids

When used in the therapeutic treatment of disease, an appropriate dosage of an antibacterial protonated/acidified nucleic acid, or mixture thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Additionally, therapeutic dosages may also be altered depending upon factors such as the severity of infection, and the size or species of the host.

Where the therapeutic use of the presently described antibacterial nucleic acids is contemplated, the antibacterial nucleic acids are preferably administered in a pharmaceutically acceptable carrier, via oral, intranasal, rectal, topical, intraperitoneal, intravenous, intramuscular, subcutaneous, intracranial, subdermal, transdermal, intratracheal methods, or the like.

Typically, but not necessarily, the preferred formulation for a given antibacterial nucleic acid is dependant on the location in a host where a given infectious organism would be expected to initially invade, or where a given infectious organism would be expected to colonize or concentrate. For example, topical infections are preferably treated or prevented by formulations designed for topical application. For example, in a preferred embodiment, the acidified nucleic acid is formulated in a water, ethanol, and propylene glycol base for topical administration. Alternately, where the targeted pathogen colonizes the stomach gut, preparations of acid stable protonated/acidified nucleic acids may be provided by oral dosing. Additionally, pulmonary infections may be treated both parenterally and by direct application of suitably formulated forms of the antibacterial nucleic acids to the lung by inhalation therapy or intranasal administration.

Where suitably formulated nucleic acids are administered parenterally, the nucleic acids can accumulate to relatively high levels in the kidneys, liver, spleen, lymph glands, adrenal gland, aorta, pancreas, bone marrow, heart, and olivary glands. Nucleic acids also tend to accumulate to a lesser extent in skeletal muscle, bladder, stomach, esophagus, duodenum, fat, and trachea. Still lower concentrations are typically found in the cerebral cortex, brain stem, cerebellum, spinal cord, cartilage, skin, thyroid, and prostate (see generally Crooke, 1993, *Antisense Research and Applications,* CRC Press, Boca Raton, Fla.). Interestingly, pathogenic bacteria also tend to accumulate in many of the above organs. Consequently, the presently described antibacterial nucleic acids can be used to target bacterial infections in specific target organs and tissues.

Preferably, animal hosts that may be treated using the nucleic acids of the present invention include, but are not limited to, invertebrates, vertebrates, birds, mammals such as pigs, goats, sheep, cows, dogs, cats, and particularly humans. The presently described protonated/acidified antibacterial nucleic acids are also contemplated to be effective in combating bacterial contamination of laboratory cultures, consumables (food or beverage preparations), or industrial processes.

Given that bacterial infection is a particularly problematic complication in immuno-compromised individuals, such as patients suffering from acquired immuno-deficiency disease syndrome (AIDS), HIV infected individuals, patients undergoing chemotherapy or radiation therapy, etc., an additional embodiment of the presently described invention is the use of the presently described antibacterial nucleic acids to treat immuno-compromised patients.

Another embodiment of the presently described invention is the use of a therapeutic nucleic acid that has a viral, cancer, fungal or other target, wherein the nucleic acid is additionally protonated/acidified so it can also serve as an antibacterial nucleic acid. The oligo will continue to address its primary target, but in addition it will then function as an antibacterial agent.

Examples of bacterial organisms against which the methods of the invention are effective include gram positive bacteria, gram negative bacteria, acid fast bacteria, *Staphylococcus aureus, Streptococcus pyogenes, Streptococcus pneumoniae* and *Escherichia coli.* The methods of the invention are effective against infection by all bacterial organisms, including members of the following genera: Aerococcus, Listeria, Streptomyces, Chlamydia, Actinomadura, Lactobacillus, Eubacterium, Arachnia, Mycobacterium, Peptostreptococcus, Staphylococcus, Corynebacterium Erysipelothrix, Dermatophilus, Rhodococcus, Ribodobacterium, Pseudomonas, Streptococcus, Bacillus, Peptococcus, Pneumococcus, Micrococcus, Neisseria, Klebsiella, Kurthia, Nocardia, Nocardiopsis, Serratia, Rothia, Escherichia, Propionibacterium, Actinomyces, Helicobacter, Enterococcus, Shigella, Vibrio, Clostridia, Salmonella, Yersinia, and Haemophilus.

Pharmaceutical Compositions and Delivery

The presently described protonated/acidified antibacterial nucleic acids may be formulated with a variety of physiological carrier molecules. The presently described antibacterial nucleic acids may also be complexed with molecules that enhance their ability to enter the target cells. Examples of such molecules include, but are not limited to, carbohydrates, polyamines, amino acids, peptides, lipids, and molecules vital to bacterial growth. For example, the antibacterial nucleic acids may be combined with a lipid, cationic lipid, or anionic lipid (which may be preferred for protonated/acidified nucleic acids). The resulting nucleic acid/lipid emulsion, or liposomal suspension may, inter alia, effectively increase the in vivo half-life of the nucleic acid. Examples of suitable anionic lipids for use with protonated/acidified nucleic acids include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol. The use of cationic, anionic, and/or neutral lipid compositions or liposomes is generally described in International Publications Nos. WO90/14074, WO 91/16024, WO 91/17424, and U.S. Pat. No. 4,897,355, herein incorporated by reference. By assembling the antibacterial nucleic acids into lipid-associated structures, the protonated/acidified antibacterial nucleic acids may be targeted to specific bacterial cell types by the incorporation of suitable targeting agents (i.e., specific antibodies or receptors) into the nucleic acid/lipid complex.

Pharmaceutical compositions containing the nucleic acids of the invention in admixture with a pharmaceutical carrier can be prepared according to conventional pharmaceutical compounding techniques. The carrier may take a wide variety of forms depending on the form of the preparation desired for administration, e.g., intravenous, oral, topical, aerosol (for topical or pulmonary delivery), suppository, parenteral, or spinal injection.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated and enteric-coated by standard techniques. Oral dosage forms of antibacterial nucleic acids will be particularly useful for the treatment of bacterial infections of the gastrointestinal tract and ulcers caused by bacterial infection (e.g., *Heliobacter pylori* infection, and the like).

For parenteral application by injection, preparations may comprise an aqueous solution of a water soluble, or solubilized, and pharmaceutically acceptable form of the antibacterial nucleic acid in an appropriate saline solution. Injectable suspensions may also be prepared using appropriate liquid carriers, suspending agents, agents for adjusting the isotonicity, preserving agents, and the like. Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference. The presently described nucleic acids should be parenterally administered at concentrations below the maximal tolerable dose (MTD) established for the antibacterial nucleic acid.

For topical administration, the carrier may take a wide variety of forms depending on the preparation, which may be a cream, dressing, gel, lotion, ointment, or liquid.

Aerosols can be prepared by dissolving or suspending the nucleic acid in a propellant such as ethyl alcohol or in propellant and solvent phases. The pharmaceutical compositions for topical or aerosol form will generally contain from about 0.01% by weight (of the nucleic acid) to about 40% by weight, preferably about 0.02% to about 10% by weight, and more preferably about 0.05% to about 5% by weight depending on the particular form employed.

Suppositories are prepared by mixing the nucleic acid with a lipid vehicle such as theobroma oil, cacao butter, glycerin, gelatin, or polyoxyethylene glycols.

The presently described antibacterial nucleic acids may be administered to the body by virtually any means used to administer conventional antibiotics. A variety of delivery systems are well known in the art for delivering bioactive compounds to bacteria in an animal. These systems include, but are not limited to, intravenous or intramuscular or intra-tracheal injection, nasal spray, aerosols for inhalation, and oral or suppository administration. The specific delivery system used depends on the location of the bacteria, and it is well within the skill of one in the art to determine the location of the bacteria and to select an appropriate delivery system.

The nucleic acids of the invention have the advantage that they are very non-toxic in all forms of administration. For example, parenteral administration of a solution of oligonucleotide of the invention was shown to be nontoxic in mice at 10 mg/mouse, which is an $LD_{50}$ of less than one at 400 mg/Kg.

Cosmetic use of Antibacterial Nucleic Acids

The protonated/acidified nucleic acids of the invention may be used in cosmetic products such as lotions, creams, topical solutions. The nucleic acids of the invention may be used both as an antibacterial agent, such as in a lotion, and as a preservative to prevent and/or retard growth of bacteria in the cosmetic preparation. Thus, the nucleic acids may be used with any known cosmetic preparation, provided the composition of the preparation is sufficiently low in pH to retain the activity of the protonated nucleic acid, i.e. 7.0 or below. The nucleic acids are present in an amount sufficient to have an antibacterial effect, and preferably between 0.25 wt % and 10.0 wt %, more preferably between 0.5 wt % and 5.0 wt%.

The cosmetic composition of the invention may contain any of a number of additives that are themselves active ingredients, such as a glycolic or alpha-hydroxy acids, vitamin A palmitate (retinyl palmitate) and/or vitamin E acetate (tocopheryl acetate). Each of these is preferably present in an amount from about 0.5 wt. % to about 5 wt %. In addition, a UV absorbing or blocking material, such as PABA, may be used.

Other compounds may also be added to have additional moisturizing effects and to improve the consistency of the composition. Examples of such compounds include, but are not limited to: certyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat Nos. 5,153,230 and 4,421,769, which are both incorporated herein by reference. If it is desirable for the composition to have additional cleaning effects, chemicals such as sodium laurel sulfate or a metal salt of a carboxylic acid may be added.

The nucleic acids of the invention may be especially useful in topical anti-acne compositions, since they have good efficacy against a broad spectrum of bacteria, they have low skin irritation, and they are chemically stable. Such compositions are preferably aqueous, as oil-based compositions may exacerbate the acne condition.

A wide variety of nonvolatile emollients are useful herein, nonlimiting examples of which are listed in *McCutcheon's*, Vol. 2 *Functional Materials*, North American Edition, (1992), pp. 137–168, which is incorporated herein by reference in its entirety, and *CTFA Cosmetic Ingredient Handbook*, Second Edition (1992) which lists Skin-Conditioning Agents at pp. 572–575 and Skin Protectants at p. 580, which is also incorporated herein by reference in its entirety.

Among the nonvolatile emollient materials useful herein especially preferred are silicones, hydrocarbons, esters and mixtures thereof.

Examples of silicone emollients include polyalkylsiloxanes, cyclic polyalkylsiloxanes, and polyalkylarylsiloxanes. The polyalkylsiloxanes useful herein include, for example, polyalkylsiloxanes with viscosities of from about 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes and a boiling point of 172° C., which primarily contains the cyclomethicone tetramer (i.e., n=4), Dow Corning® 344 fluid having a viscosity of 2.5 centistokes and a boiling point of 178° C., which primarily contains the cyclomethicone pentamer (i.e., n=5), Dow Corning® 245 fluid having a viscosity of 4.2 centistokes and a boiling point of 205° C., which primarily contains a mixture of the cyclomethicone tetramer and pentamer (i.e., n=4 and 5), and Dow Corning® 345 fluid having a viscosity of 4.5 centistokes and a boiling point of 217° C., which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g., Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Hydrocarbons useful herein include straight and branched chain hydrocarbons having from about 10 to about 30 carbon atoms, more preferably from about 12 to about 24 carbon atoms, and most preferably from about 16 to about 22 carbon atoms. Nonlimiting examples of these hydrocarbon materials include dodecane, squalane, cholesterol, hydrogenated polyisobutylene, docosane (i.e., a $C_{22}$ hydrocarbon), hexadecane, isohexadecane (a commercially available hydrocarbon sold as Permethyl® 101A by Presperse, South Plainsfield, N.J.). Other hydrocarbon materials useful herein include paraffins and mineral oils such as USP light mineral oil (e.g., Klearol® available from Witco Corp., Melrose Park, Ill.) and USP heavy mineral oil (e.g., Klearol® available from Witco Corp., Melrose Park, Ill.).

Also useful as nonvolatile emollients are esters, including esters of monofunctional and difunctional fatty acids that have been esterified with alcohols and polyols (i.e., alcohols having two or more hydroxy groups). A wide variety of esters are useful herein, with long chain esters of long chain fatty acids being preferred (i.e., C10–40 fatty acids esterified with C10–40 fatty alcohols). Nonlimiting examples of esters useful herein include those selected from the group consisting of diisopropyl adipate, isopropyl myristate, isopropyl palmitate, myristyl propionate, ethylene glycol distearate, 2-ethylhexyl palmitate, isodecyl neopentanoate $C_{12-15}$ alcohols benzoate, di-2-ethylhexyl maleate, cetyl palmitate, myristyl myristate, stearyl stearate, cetyl stearate, behenyl behenrate, and mixtures thereof.

Use of Antibacterial Nucleic Acids in Disinfectants

The nucleic acids of the invention may also find use as disinfectants, and particularly as liquid disinfectant preparations having biostatic or preferably biocidal properties. The disinfectant solution contains at least a sufficient amount of nucleic acid of the invention, and may also contain other active ingredients with biostatic and/or biocidal properties. For example, the disinfectant may contain nucleic acids of the invention with a suitable concentration of a quaternary ammonium compound such as: dimethylbenzyldodecylammonium chloride, dimethylbenzyl decylammonium chloride, dimethylbenzyl decylammonium bromide, dimethylbenzylloctylammonium chloride, and cocosalkyldimethylbenzylammonium chloride.

In another example, suitable microbicidal biguanidine compounds, such as oligohexamethylene biguanide salts and bisbiguanides, can be used. See, e.g., U.S. Pat. No. 5,030,659 which is incorporated herein by reference. Additional biocidal ingredients include aldehydes, phenol derivatives, and halogen phenyl derivatives. See, e.g., U.S. Pat. No. 5,767,054, which is incorporated herein by reference. Other compounds with such activity, as will be recognized by those skilled in the art, may also be used in conjunction with the nucleic acid of the invention.

In addition to the described active components, the disinfectant preparations of the invention may contain other typical components depending on the desired use of the formulation. In particular, an acidifier may be used to keep the pH range of the disinfection solution below 7. Suitable solvents for the nucleic acids and/or the other active ingredients may be employed, and preferably are water or water miscible organic solvents. Solutions such as these may be readily sprayed using compressed air or any other propellants known by those in the art.

These preparations of the invention are especially suitable for surface disinfection in medically-related environments, such as hospitals, veterinary clinics, dental and medical offices and the like. Use of solutions of the invention in the sterilization of surgical instruments is especially preferred. These preparations are also useful in public areas such as schools, public transport, restaurants, hotels and laundries. The disinfectants also find use in home as sanitizers for toilets, basins, and kitchen areas.

The protonated/acidified nucleic acids of the invention may also be used in disinfection solutions for skin. Such compositions contain the nucleic acid of the invention in a solution that is in a vehicle suitable for topical use. The disinfectant may be of the quick-drying variety, in which case it is desirable for the nucleic acid to be in an ethanol base. Such solutions preferably contain an emollient for the skin as well, since the alcohol tends to be extremely drying to skin. Examples of suitable emollients include, but are not limited to: a polyhydric alcohol such as polyethylene glycol, glycerin, diglycerin, propylene glycol, butylene glycol, erythritol, dipropylene glycol, and sorbitol. The amount of emollient may be in the range of 0.1–3.0 w/w %, and more preferably in the range 0.2–1.5 w/w %. In the case where the content of the emollient is less than 0.1 wt % it may not be very effective, and over 3.0% the solution may be overly sticky.

Disinfectant solutions for the skin are especially useful in disinfection of hands following medical treatment or waste management. Disinfection may also be useful in surgical settings, both for the medical staff and to sterilize the area of surgery on the patient.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade, and pressure is at or near atmospheric.

Example 1
Synthesis of Nucleic Acids

Nucleic acids were synthesized using commercial phosphoramidites on commercially purchased DNA synthesizers from <1 uM to >1 mM scales using standard phosphoramidite chemistry and methods that are well known in the art, such as, for example, those disclosed in Stec et al., 1984, *J. Am. Chem. Soc.* 106:6077–6089, Stec et al., 1985, *J. Org. Chem.* 50(20):3908–3913, Stec et al., 1985, *J. Chromatog.* 326:263–280, LaPlanche et al., 1986, *Nuc. Acid. Res.* 14(22):9081–9093, and Fasman, 1989, *Practical Handbook of Biochemistry and Molecular Biology*, CRC Press, Boca Raton, Fla., herein incorporated by reference.

Nucleic acids were deprotected following phosphoramidite manufacturer protocols. Unpurified nucleic acids were either dried down under vacuum or precipitated and then dried. Sodium salts of nucleic acids were prepared using the commercially available DNA-Mate (Barkosigan Inc.) reagents or conventional techniques such as commercially available exchange resin, e.g., Dowex (Dupont), or by addition of sodium salts followed by precipitation, diafiltration, or gel filtration, etc. or were incorporated into the purification procedure.

Example 2
Purification of Nucleic Acids

A variety of standard methods were used to purify/produce the presently described antibacterial nucleic acids. In brief, antibacterial nucleic acids were purified by chromatography on commercially available reverse phase (for example, see the RAININ Instrument Co., Inc. instruction manual for the DYNAMAX®-300A, Pure-DNA reverse phase columns, 1989, or current updates thereof, herein incorporated by reference) or ion exchange media such as Waters' Protein Pak or Pharmacia's Source Q (see generally, Warren and Vella, 1994, "Analysis and Purification of Synthetic Nucleic Acids by High-Performance Liquid Chromatography", in *Methods in Molecular Biology*, vol. 26; *Protocols for Nucleic Acid Conjugates*, S. Agrawal, ed. Humana Press, Inc., Totowa, N.J.; Aharon et al., 1993, *J. Chrom.* 698:293–301; and Millipore Technical Bulletin, 1992, *Antisense DNA: Synthesis, Purification, and Analysis*). Peak fractions were combined and the samples were concentrated and desalted via alcohol (ethanol, butanol, isopropanol, and isomers and mixtures thereof, etc.) precipitation, reverse phase chromatography, diafiltration, or gel filtration.

Example 3
Protonation/Acidification of Nucleic Acids

Subsequently, or during the above steps, protonated/acidified forms of the described nucleic acids can be generated by subjecting the purified, partially purified, or crude nucleic acids, to a low pH (e.g., acidic) environment. Purified or crude nucleic acids were protonated/acidified with acid, including phosphoric acid, nitric acid, hydrochloric acid, and acetic acid.

Pooled fractions of a strong anion exchange (SAX)-purified oligonucleotide (at approximately 2–25 $A_{260}$ per ml) were pumped onto a PRP (Hamilton Co.) column. This was followed immediately with an excess of dilute acid (e.g., 25 mM HCl) until the eluent was acidic. The column was then washed with purified water (no salt or buffers) until the conductivity and pH of the eluent returned to essentially background levels. The oligonucleotide was then dried down in a commercially available vacuum evaporator. Alternatively, the oligonucleotide was suspended in dilute acid and either chromatographed over the PRP or similar column as described above, or chromatographed over a size exclusion column (e.g., BioRad Biogel P2 or P4) using water as solvent. Alternatively, a desalted nucleic acid may be dissolved in alkaline salt solution (e.g., 0.4 M NaCl and pH 12, 25 mM NaOH), run on a PRP column, washed with acid followed by water, and then eluted, as described above. Alternatively, a nucleic acid may be chromatographed over a cation exchange column that is in the H+ form, collected and dried down as described above.

Nucleic acids were also acidified by adding an acid, e.g., HCl (0.1 N), directly to a nucleic acid solution (approximately 300 $A_{260}$ per ml) until the pH of the solution reached pH 1 to pH 3. The acidified nucleic acids can then be run over an acid stable size exclusion column such as a BioRad Biogel P2 or P4 column.

Lyophilized or dried-down preparations of nucleic acids to be used in bacterial experiments were dissolved in pyrogen-free, sterile, physiological saline (i.e., 0.85% saline), sterile Sigma water, and filtered through a 0.45 micron Gelman filter (or a sterile 0.2 micron pyrogen-free filter prior to animal studies).

When suspended in water or saline, the nucleic acid preparations typically exhibited a pH between 1 and 4.5 depending upon the level of protonation/acidification, which is determined by how much acid is used in the acidification process.

Example 4
Bacterial Growth Studies
Limited Nutrient Growth Study

For the limited nutrient growth study, cells were taken off plates and suspended in PBS to give a final concentration of $10^5$ CFU/ml and a final volume of 1 ml. Mueller-Hinton broth was added(40 µl for *S. aureus* ACC # 13301, 20 µl for *P. aeruginosa* ACC # 10145). 100 µl of water or 100 µl of nucleic acid (32 $A_{260}$ units, 2'-O-methyl ribonucleotides, phosphodiester linkage, 5' and 3' inverted T end-blocked, sequence CGCCATTGG, SEQ ID NO: 1) was added and the tubes were incubated at 35° C. without shaking for approximately 24 hours. The $A_{625}$ was measured and the percent inhibition calculated as a percent of the control. The results are in the following table:

| Bacteria | pH of Nucleic Acid | Inhibition of Growth (%) |
| --- | --- | --- |
| S. aureus | Water Control-pH 7 | 0 |
| S. aureus | 2 | 100 |
| S. aureus | 3 | 100 |
| S. aureus | 4 | 100 |
| S. aureus | 5 | 16 |
| S. aureus | 7 | 0 |
| P. aeruginosa | Water Control-pH 7 | 0 |
| P. aeruginosa | 2 | 100 |
| P. aeruginosa | 3 | 100 |
| P. aeruginosa | 4 | 100 |
| P. aeruginosa | 5 | 0 |
| P. aeruginosa | 7 | 0 |

Stationary Growth Study

A stationary growth assay was also performed to study the effect of pH on the anti-bacterial activity of nucleic acids. Cells were taken off plates and suspended in saline to give a final concentration of $10^7$ CFU/ml of *S. aureus* in 1 ml of PBS. 100 μl of water or 100 μl of nucleic acid (32 $A_{260}$ units, 2'-O-methyl ribonucleotides, phosphodiester linkage, 5' and 3' inverted T end blocked, sequence CGCCATTGG, SEQ ID NO: 1) was added and the tubes were incubated at 35° C. without shaking for approximately 24 hours. Aliquots were plated directly or after dilutions and incubated at 37° C. and colonies counted after 24 hours. The results are in the following table:

| Bacteria | pH of Nucleic Acid | CFU/ml |
| --- | --- | --- |
| *S. aureus* | Water Control-pH 7 | $10^7$ |
| *S. aureus* | 2 | 0 |
| *S. aureus* | 3 | $10^3$ |
| *S. aureus* | 4 | $10^6$ |
| *S. aureus* | 5 | $10^7$ |
| *S. aureus* | 7 | $10^7$ |

From these results, it was concluded that lowering the pH of a nucleotide conferred upon it bactericidal and bacteriostatic effects. Next, the effect of sequence identity and length were explored.

Example 5
Sequence Effects on Antibacterial Activity

First, a stationary growth assay was performed to study the effect of sequence length. Cells were taken off plates and suspended in saline to give a final concentration of $10^7$ CFU/ml of Strep. mutans in 1 ml of PBS. 50 μl of water or 50 μl of nucleic acids of varying length (16 $A_{260}$ units) were added and the tubes incubated at 35° C. without shaking for approximately 24 hours. Each of the nucleic acids used consisted of 2'-O-methyl substituted ribonucleotides phosphodiester linked with 5' and 3' inverted T end-blocking. The sequences were: 114.6-CGCCAT (SEQ ID NO: 2); 114.12-ACGCGCCATTGG (SEQ ID NO: 3); 114.21-GGAACGCGCCATTGGTATATC (SEQ ID NO: 4). The lengths reported in the following table for each nucleic acid include the inverted T's at the 5' and 3' ends. Aliquots were plated directly or after dilutions and incubated at 37° C. and colonies counted after 24 hours. The results are in the following table:

| Bacteria | Nucleic Acid | Length (Bases) | pH | Inhibition (%) | CFU/ml |
| --- | --- | --- | --- | --- | --- |
| Strep. mutans | Water Control | 0 | 7 | 0 | $10^7$ |
| Strep. mutans | 114.6 | 8 | 3 | 100 | 0 |
| Strep. mutans | 114.12 | 14 | 3 | 100 | 0 |
| Strep. mutans | 114.21 | 23 | 3 | 100 | 0 |
| Strep. mutans | 114.6 | 8 | 7 | 0 | $10^7$ |
| Strep. mutans | 114.12 | 14 | 7 | 0 | $10^7$ |
| Strep. mutans | 114.21 | 23 | 7 | 0 | $10^7$ |

Next, a limited nutrient growth assay was performed to study the effects of nucleotide homopolymers (AAAAAAAAAAAA, SEQ ID NO: 5; UUUUUUUUUUUU, SEQ ID NO: 6; GGGGGGGGGGGG, SEQ ID NO: 7; CCCCCCCCCCCC, SEQ ID NO: 8). Each homopolymer used consisted of 2'-O-methyl substituted ribonucleotides phosphodiester linked, with both 3' and 5' butanol end-blocking. Cells were taken off plates and suspended to give a final concentration of $10^5$ CFU/ml in 1 ml of PBS. Mueller-Hinton broth was added (40 μl for *S. aureus* ACC # 13301, 20 μl for *P. aeruginosa* ACC # 10145). 100 μl of water or 100 μl of nucleic acid at pH 1.5 (32 $A_{260}$ units) were added and the tubes were incubated at 35° C. without shaking for approximately 24 hours. The $A_{625}$ was measured and the percent inhibition calculated as a percent of the control. The results are in the following table:

| Bacteria | Oligonucleotide, pH 1.5 | Inhibition (%) |
| --- | --- | --- |
| *S. aureus* | Water Control-pH 7 | 0 |
| *S. aureus* | Homopolymer, 12 A | 100 |
| *S. aureus* | Homopolymer, 12 C | 100 |
| *S. aureus* | Homopolymer, 12 G | 100 |
| *S. aureus* | Homopolymer, 12 U | 100 |
| *P. aeruginosa* | Water Control-pH 7 | 0 |
| *P. aeruginosa* | Homopolymer, 12 A | 100 |
| *P. aeruginosa* | Homopolymer, 12 C | 100 |
| *P. aeruginosa* | Homopolymer, 12 G | 100 |
| *P. aeruginosa* | Homopolymer, 12 U | 100 |

Next, a limited nutrient growth assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended to give a final concentration of $10^5$ CFU/ml in 1 ml of PBS. Mueller-Hinton broth was added (40 μl for *S. aureus* ACC # 13301, 20 μl for *E. coli* ACC # 35218). 25 μl of water or 25 μl of nucleic acid at pH 1.5 (8 $A_{260}$ units) were added and the tubes were incubated at 35° C. without shaking for approximately 24 hours. The $A_{625}$ was measured and the percent inhibition calculated as a percent of the control. Aliquots were plated directly or after dilutions and incubated at 37° C. and colonies counted after 24 hours to determine CFUs. The results are in the following table:

| Bacteria | Nucleic Acid | Length (Bases) | Inhibition (%) | CFU/ml |
| --- | --- | --- | --- | --- |
| *S. aureus* | Water Control | 0 | 0 | $10^6$ |
| *S. aureus* | G | 1 | 100 | $10^3$ |
| *S. aureus* | U | 1 | 100 | $10^2$ |
| *S. aureus* | GU | 2 | 100 | $10^3$ |
| *S. aureus* | AUG | 3 | 100 | $10^3$ |
| *S. aureus* | 114.12 | 12 | 100 | $10^3$ |
| *E. coli* | Water Control | 0 | 0 | $10^8$ |
| *E. coli* | G | 1 | 100 | $10^3$ |
| *E. coli* | U | 1 | 100 | $10^2$ |
| *E. coli* | GU | 2 | 100 | $10^3$ |
| *E. coli* | AUG | 3 | 100 | $10^4$ |
| *E. coli* | 114.12 | 12 | 100 | $10^3$ |

A stationary phase assay was performed to study the effects of monomers, dimers and trimers. Each nucleic acid used consisted of 2'-O-methyl substituted ribonucleotides phosphodiester linked, with both 3' and 5' blocking with butanol. The nucleic acid designated 114.12 had a sequence of ACGCGCCATTAT, SEQ ID NO: 9. Cells were taken off plates and suspended in saline to give an $A_{625}$ of 0.08 for *S. aureus*, 0.12 for *E. coli*, and 0.1 for *K. pneumoniae* in 1 ml of PBS. 25 μl of water or 25 μl of nucleic acid (8 $A_{260}$ units) were added and the tubes incubated at 35° C. without shaking for approximately 24 hours. Aliquots were plated directly or after dilutions and incubated at 37° C. and colonies counted after 24 hours to determine CFUs. The results are in the following table:

| Bacteria | Nucleic Acid | Length (Bases) | CFU/ml |
|---|---|---|---|
| S. aureus | Water Control | 0 | $10^6$ |
| S. aureus | G | 1 | 0 |
| S. aureus | U | 1 | 0 |
| S. aureus | GU | 2 | 0 |
| S. aureus | AUG | 3 | 0 |
| S. aureus | 114.12 | 12 | 0 |
| E. coli | Water Control | 0 | $10^7$ |
| E. coli | G | 1 | 0 |
| E. coli | U | 1 | 0 |
| E. coli | GU | 2 | 0 |
| E. coli | AUG | 3 | 0 |
| E. coli | 114.12 | 12 | 0 |
| K. pneumoniae | Water Control | 0 | $10^8$ |
| K. pneumoniae | G | 1 | $10^2$ |
| K. pneumoniae | U | 1 | $10^1$ |
| K. pneumoniae | GU | 2 | $10^1$ |
| K. pneumoniae | AUG | 3 | $10^1$ |
| K. pneumoniae | 114.12 | 12 | $10^2$ |

In conclusion, these results demonstrate that the ability of protonated/acidified nucleic acids to function as an antibacterial agent is independent of sequence identity. Futhermore, homopolymers and nucleic acids as short as monomers are also effective. These results indicate that although sequence may play a role in the activity of the oligonucleotide, there is also another mechanism of the anti-bacterial effect which is not antisense dependent, and is thus sequence independent.

Example 6
In Vivo Assays

Several examples are provided of in vivo studies to determine the efficacy of the present invention as an antibacterial agent. The following experiments focus on topical skin and the outer ear epidermis, as well as examples of systemic treatment for sepsis.
Efficacy in Topical Skin Bacterial Infections Skin boils, called furuncles, were treated with protonated/acidified nucleic acids. A furuncle is a localized pyogenic infection typically originating in a hair follicle. A furuncle is a round, tender, pus-filled area of the skin, developing a white cap which will rupture if stressed. Often, a furuncle may be an infection of the hair follicle in the deepest section. A furuncle will normally heal in 10–25 days. Without treatment, furuncles usually must drain before they will heal. This most often occurs in just under 2 weeks. If the furuncle is a deep lesion, it may require systemic antibiotic therapy to eliminate the bacteria in addition to minor surgery to open the furuncle and drain the pus. In summary, furuncles are painful swellings of the skin caused by deep skin infection with bacteria, that rarely resolve untreated in less than 10 days.
Protonated/Acidified Nucleic Acids' Efficacy in Treatment Of Staphylococcal Furuncles Protonated/acidified nucleic acids have demonstrated efficacy in treating a 1.5 cm furuncle on the back of a 36-year-old male subject in good health. Within 8 hours, the protonated/acidified nucleic acids rapidly and dramatically relieved both the pain and swelling of the furuncle.

Protonated/acidified nucleic acid (pH 1.5, sequence ACGCGCCATTAT, SEQ ID NO: 9) was used to treat a 1.5 cm furuncle one day after its appearance. The nucleic acid consisted of 2'-O-methyl substituted ribonucleotides, phosphodiester linked, end blocked with an inverted T at both the 5' and 3' ends. Specifically, 100 µl of protonated/acidified nucleic acids were dissolved in water (18.9 mMolar) to treat the 1.5 cm furuncle, which was raised, red and swollen, with a 2–3 mM pustule, and was very painful to the subject. After 8 hours of treatment, the furuncle had spontaneously drained and was significantly reduced to approximately 0.5 cm in size with a concurrent reduction in swelling and redness. The subject's pain was significantly alleviated. A second 50 µl application of protonated/acidified nucleic acids was applied at this time.

After 16 hours from the initial treatment, there was virtually no swelling, pain, or inflammation. A small pinkish area of <0.5 cm remained from the original furuncle. A final application of protonated/acidified nucleic acids was applied, 24 hours post treatment of the infection, to continue accelerating the healing process. The residual vestiges of the furuncle healed on their own after the third application and within a day.

In conclusion, protonated/acidified nucleic acids have been demonstrated to be very effective in rapidly treating a Staphylococcal furuncle and using water as the transport medium. Protonated/acidified nucleic acids were particularly effective in rapidly resolving both the pain and swelling of the furuncle.
Efficacy in Topical Treatment of Ear Infections Protonated/acidified nucleic acids were very effective in treating outer ear epidermal infections in chinchillas caused by Pseudomonas aeruginosa bacteria. All the chinchilla infected ears that received continued protonated/acidified nucleic acid treatment were completely cured 4 days after treatment began.

Chinchillas' ears were infected with Pseudomonas aeruginosa bacteria. Specifically, the maceration of the epidermal layer of the chinchillas' ears was caused by prolonged exposure of the ears to water. This helps create a receptive environment for the Pseudomonas infection in the epidermal layer of skin lining in the chinchillas' ear canals. Cotton plegets were saturated with a suspension of washed Pseudomonas aeruginosa and were inserted in the ear canals of the chinchillas. The plegets were removed after 48 hours.

Treatment of the chinchillas began on day 3 post infection, when the ears were judged to have a "level 3" severity as determined by otoscopic examination. The chinchillas received two daily topical applications of either 400 µl of protonated/acidified nucleic acids at pH 1.5 of sequence ACGCGCCATTAT, SEQ ID NO: 9, in water (2.8 mMolar) or 400 µl of the protonated/acidified nucleic acids of identical sequence (2 mMolar) in a vehicle mixture (water/ethanol/propylene glycol). The nucleic acid consisted of 2'-O-methyl substituted ribonucleotides, phosphodiester linked and end blocked with butanol at both the 5' and 3' ends. The chinchillas were examined daily to assess the effectiveness of treatment based on the degree of severity of the ear infections.

The results of the protonated/acidified nucleic acid treatment indicated that all of the treated chinchillas' ears showed a significant reduction in the severity of ear infections, as determined by otoscopic examination. Significant improvements could be observed after 3 treatments of protonated/acidified nucleic acids. The chinchillas received treatment for an additional 4 to 5 days. Untreated control chinchillas showed no improvement over this time frame. In contrast, all ear infections that received continued protonated/acidified nucleic acids treatment were completely cured by day 7 post infection (i.e., 4 days after treatment began with protonated/acidified nucleic acids).

In addition, there were slight differences in the progression of healing between protonated/acidified nucleic acids dissolved in the two transport mediums, water or the vehicle mixture (water/ethanol/propylene glycol). Based on otoscopic examination, protonated/acidified nucleic acids in the vehicle mixture were slightly more effective in treating the ear infections.

In conclusion, protonated/acidified nucleic acids have demonstrated effectiveness in treating chinchillas' outer ear infections caused by *Pseudomonas aeruginosa*. This is significant since this infectious bacteria is naturally an antibiotic-resistant bacteria.

Efficacy in Treatment of Strep. pyogenes Skin Infection on a Dog

A 135 lb. 2 year old, female Newfoundland had sustained a cut on her abdomen and developed a Strep. pyogenes infection. The area was swollen, inflamed and painful to the touch. Treatment with Neosporin® (Warner-Lambert, Co.) for 3 days failed to produce any improvement. Two treatments, separated by 12 hours, directly to the injury with 2'-O-methyl substituted ribonucleotides that were phosphodiester linked, pH 1.5, end blocked with butanol at both the 5' and 3' ends, with sequence of ACGCGCCATTAT (SEQ ID NO: 9), completely cleared up the infection, swelling, inflammation, and sensitivity to touch.

Protonated/Acidified Nucleic Acid Efficacy in a Topical Pseudomonas Burn Model of Infection Protonated/acidified nucleic acids have demonstrated efficacy in treating topical skin infections in immuno-compromised mice. Mice were treated with cyclophosphamide (200 mg/kg, I.P.) in advance of a burn to the skin to inhibit their immune systems. Three days later burns were induced, followed by application of $10^9$ CFU of *Pseudomonas aeruginosa* topically applied to the burn site to create an infection. Treatment with nucleic acid occurred at 4 hrs. and 8 hrs. post infection. The nucleic acid used in the experiment was at pH 1.5, had the sequence ACGCGCCATTAT, SEQ ID NO: 9, and consisted of 2'-O-methyl substituted ribonucleotides, phosphodiester linked and end blocked with butanol at both the 5' and 3' ends. One hundred percent (100%) of the treated animals survived and were free of systemic Pseudomonas infections while 90% of the control animals developed systemic infections and died. The protonated/acidified nucleic acids were able to cure the topical infection. In addition, topical application of nucleic acids were able to prevent the topical Pseudomonas infection from progressing to a fatal, systemic infection.

Protonated/Acidified Nucleic Acid Efficacy in a Systemic Pseudomonas Burn Model of Infection Mice were treated S.C. with $10^6$ or $10^7$ CFU of *Pseudomonas aeruginosa* after induction of a skin burn. Two hours post infection, treatment was initiated with acidified nucleic acid. Forty percent (40%) of the dose was administered I.V. with the remainder given S.C. The nucleic acid used in the experiment was at pH 1.5, had the sequence ACGCGCCATTAT, SEQ ID NO: 9, and consisted of 2'-O-methyl substituted ribonucleotides, phosphodiester linked and end blocked with butanol at both the 5' and 3' ends. The procedure was repeated 6 hrs. later. Additional subcutaneous injections were given twice daily on day two and three. All of the 45 control animals died, and 100% of the 40 treated mice survived and were healthy. These treated, healthy mice were sacrificed and checked for sepsis. Pseudomonas bacteria were not detected in the spleen, liver, or blood.

In conclusion, a protonated/acidified nucleic acid was 100% effective at treating a systemic Pseudomonas infection that would have been fatal if left untreated.

Example 7
Toxicity of Protonated/Acidified Nucleic Acids

Forty five animals (mice, male/C57 Balb/c) received protonated/acidified nucleic acid treatment subcutaneous, intraperitoneal injection, or topical application. The mice were randomly chosen and were approximately 6 to 8 weeks of age at study commencement (25–30 gm. body weight). The mice were housed five to a box and maintained in an environmentally controlled room with free access to food and water.

The mice (five per group) were injected daily for 14 days with a protonated/acidified nucleic acid at pH 1.5 of sequence ACGCGCCATTAT, SEQ ID NO: 9, or water. The nucleic acid consisted of 2'-O-methyl substituted ribonucleotides, phosphodiester linked, end blocked with butanol at both the 5' and 3' ends. Treatment was via intraperitoneal administration, subcutaneous administration, or was administered topically.

All mice were observed daily for viability and signs of toxicity during the treatment period. Necropsies were performed 24 hours after the last injection. At necropsy, a complete examination of all body cavities and organs was conducted. Selected organs were fixed and stained for histopathological evaluation. The summary of the findings are as follows.

Mortality and Clinical Manifestations

During the study, all mice remained fully active and alert with no clinical signs of abnormal behavior during the course of study, even at the highest dose of 100 mg/kg.

Clinical Chemistry

Among all the clinical chemistry parameters tested, there were no abnormalities in liver enzymes (alkaline phosphatase, ALT, AST) and total bilirubin level. Mean serum alkaline phosphatase, ALT and ASL levels showed no significant differences from the vehicle control values, suggesting that there is no evidence of toxicosis. The indirect and direct bilirubin values showed no differences from those of the vehicle treated controls, indicating no renal or hepatic abnormalities.

Gross Necropsy

During the study, observation determined that there was nothing grossly evident at the site of injection suggesting no local inflammatory reactions associated with even the highest dose of nucleic acid. There were no visible signs of enlargement or necropsy of any organs. Specifically, there was no enlargement of the spleen, liver, or kidneys as compared to those of the control animals, even at doses of 100 mg/kg per day administered for 14 consecutive days.

Histopathology

Slides of the different tissues showed no differences between the control and treated animals.

In summary, the key results were:
(1) There were no significant increases in any enzyme level in the treated group vs. control group;
(2) there were no signs of gross abnormalities in any of the animals treated with oligos;
(3) all animals remained healthy and alert throughout the study; and
(4) all routes (intraperitoneal, subcutaneous, topical) provided similar results.

The results indicated that the protonated/acidified nucleic acids were non-toxic even after 14 days of daily administration of 100 mg per kilogram and regardless of the route of administration.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A modified nucleic acid polymer comprising:
a substitution at a residue of a ribose group, said substitution distinguishing said nucleic acid from naturally occurring RNA or DNA; and
a blocking chemical modification at the 3' terminus of the nucleic acid;
wherein the nucleic acid is protonated to an extent that the nucleic acid exhibits a pH in a range of about 0 to about 5 at a concentration of 1 mg/ml in water, and the nucleic acid exhibits a pH stability of at least one hour at a pH of about 1 to about 5 at 37° C., and still further wherein the nucleic acid exhibits antibacterial activity.

2. The nucleic acid of claim 1, further comprising a blocking chemical modification at the 5' terminus of said nucleic acid, wherein the nucleic acid has a nuclease resistance of at least twice that of a naturally occurring nucleic acid having the same number of nucleotides.

3. The nucleic acid molecule of claim 1, wherein the nucleic acid is comprised of about 2 to about 100 nucleotides.

4. The nucleic acid of claim 1, wherein the nucleic acid comprises internucleoside linkages completely or partially derivatized by a chemical moiety selected from the group consisting of: phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, bridged phosphorothioate linkages, sulfone internucleotide linkages, 3'-3' linkages, 2'-5' linkages, 5'-5' linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, and p-isopropyl oligonucleotides.

5. The nucleic acid of claim 1, wherein the blocking chemical modification is butanol.

6. The nucleic acid of claim 1, wherein the nucleic acid comprises 3'-5' internucleoside linkages, and wherein a 2' residue of a ribose group is substituted.

7. The nucleic acid of claim 1, wherein the nucleic acid comprises 2'-5' internucleoside linkages, and wherein a 3' residue of a ribose group is substituted.

8. The nucleic acid of claim 1, wherein the ribose substitution is an O-alkyl.

9. A composition comprising the NA of claim 8, wherein the composition is in a liquid form and wherein the composition has a pH of about 0 to 5.

10. A composition comprising the NA of claim 8, wherein the composition is a solid and wherein the composition has a pH of about 1 to 5 when dissolved at 1 mg/ml in water.

11. A composition comprising the NA of claim 8, further comprising an additive agent.

12. The composition of claim 8, wherein the nucleic acid comprises 3'-5' internucleoside linkages, and wherein a 2' residue of a ribose group is substituted.

13. The composition of claim 8, wherein the nucleic acid comprises 2'-5' internucleoside linkages, and wherein a 3' residue of a ribose group is substituted.

14. The nucleic acid of claim 1, wherein the ribose substitution is an O-alkyl-n(O-alkyl).

15. A modified nucleic acid comprising:

a nucleotide monomer, said monomer comprising a blocking chemical modification at the 5' position of the monomer; and a blocking chemical modification at the 3' position of the monomer; and one or more exogenous protons introduced to reactive sites on said monomer, wherein the nucleic acid exhibits a pH stability of at least one hour in pH of 0.01 to 5, and wherein the nucleic acid exhibits antibacterial activity.

16. The nucleic acid of claim 15, further comprising a substitution at the 2' position of said monomer, said substitution distinguishing the monomer from a naturally occurring ribonucleotide or deoxyribonucleotide.

17. The nucleic acid of claim 15, wherein the nucleic acid molecule is completely or partially derivatized by a chemical moeity selected from the group consisting of: phosphodiester linkages, phosphotriester linkages, phosphoramidate linkages, siloxane linkages, carbonate linkages, carboxymethylester linkages, acetamidate linkages, carbamate linkages, thioether linkages, bridged phosphoramidate linkages, bridged methylene phosphonate linkages, phosphorothioate linkages, methylphosphonate linkages, phosphorodithioate linkages, morpholino, bridged phosphorothioate linkages, sulfone internucleotide linkages, 3'-3' linkages, 2'-5' linkages, 5'-5' linkages, 2'-deoxy-erythropentofuranosyl, 2'-fluoro, 2'-O-alkyl nucleotides, 2'-O-alkyl-n(O-alkyl) phosphodiesters, morpholino linkages, p-ethoxy oligonucleotides, PNA linkages, and p-isopropyl oligonucleotides.

18. A composition comprising:

a nucleic acid comprising a substitution at a residue of a ribose group, a blocking chemical modification at the 3' terminus of the nucleic acid, wherein the nucleic acid is protonated to an extent that the nucleic acid exhibits a pH in a range of about 0 to about 5 at a concentration of 1 mg/ml in water; and an excipient;

wherein the composition exhibits antibacterial activity.

19. A composition comprising:

a nucleotide monomer comprising a blocking chemical modification at the 5' position of the monomer; a blocking chemical modification at the 3' position of the monomer; and one or more exogenous protons introduced to reactive sites on said monomer, wherein the nucleic acid exhibits a pH stability of at least one hour in pH of 0.01 to 5, and wherein the nucleic acid exhibits antibacterial activity.

* * * * *